United States Patent [19]
Boute

[11] Patent Number: 6,129,744
[45] Date of Patent: Oct. 10, 2000

[54] CARDIAC TREATMENT SYSTEM AND METHOD FOR SENSING AND RESPONDING TO HEART FAILURE

[75] Inventor: Willem Boute, Dieren, Netherlands

[73] Assignee: Vitatron Medical, B.V., Dieren, Netherlands

[21] Appl. No.: 08/985,127

[22] Filed: Dec. 4, 1997

[51] Int. Cl.[7] .......................... A61N 1/368; A61N 1/362; A61N 1/365

[52] U.S. Cl. .............................. 607/25; 600/517; 600/516

[58] Field of Search ........................... 607/5, 9; 600/517, 600/518, 516

[56] References Cited

U.S. PATENT DOCUMENTS

| | | |
|---|---|---|
| 4,401,120 | 8/1983 | Hartlaub et al. . |
| 4,550,370 | 10/1985 | Baker . |
| 4,556,063 | 12/1985 | Thompson et al. . |
| 4,972,834 | 11/1990 | Begemann et al. . |
| 5,014,698 | 5/1991 | Cohen . |
| 5,065,759 | 11/1991 | Begemann et al. . |
| 5,306,293 | 4/1994 | Zacouto ..................................... 607/17 |
| 5,560,368 | 10/1996 | Berger ..................................... 600/517 |
| 5,700,283 | 12/1997 | Salo . |
| 5,782,890 | 7/1998 | Wahlstrand et al. . |
| 5,792,197 | 8/1998 | Nappholz . |
| 5,902,324 | 5/1999 | Thompson et al. . |
| 6,021,351 | 2/2000 | Kadhiresan et al. . |
| 6,045,513 | 4/2000 | Stone et al. . |

OTHER PUBLICATIONS

Sharp et al., "Does Left Ventricular Dysfunction Produce a Different Pattern of AT Length Shortening?" PACE, vol. 20, Apr. 1997, Part I, p. 1232 [NASPE Abstracts, #730].

Sharp et al., "Does Left Ventricular Dysfunction Produce a Differnt Pattern of QT Length Shortening?" PACE,. vol. 20, May 1997, Part II, p. 1529 [Europace '97 Abstracts, #358].

Caseaq et al., "Four Chamber Pacing in Dilated Cardiomyopathy," PACE, vol. 17, Nov. 1994, Part II.

Sharp et al., "Non–Linearity of the Oxygen Uptake; Heart Rate Relationship in Pacemaker Patients With Left Ventricular Dysfunction," PACE, vol. 20, May 1997, Part II, p. 1530 [Europace '97 Abstracts, #362].

*Primary Examiner*—Carl H. Layno
*Attorney, Agent, or Firm*—Thomas F. Woods; Michael J. Jaro; Harold Patton

[57] ABSTRACT

A pacing system and method for determining a heart failure condition such as left ventricular dysfunction in a patient are provided, based upon obtaining information from cardiac signals, which information is processed and examined for an indication of the onset or progression of LVD. Since LVD is generally characterized by conduction disorders and other body responses calling for different heart rates during exercise, an examination of sensed cardiac signals is utilized to obtain data reflective of an LVD condition. In one embodiment, a QT rate responsive pacemaker is utilized, wherein variations in QT interval corresponding to heart rate are detected and stored, and then periodically analyzed to detect changes of sufficient magnitude to indicate onset of LVD. In another embodiment, changes in lower natural rate at nighttime or rest are monitored and analyzed for detection for a trend indicating LVD. Other cardiac signal parameters, such as T-wave amplitude changes during exercise, and QRS duration changes, can also be processed to obtain information from which LVD can be determined. When an LVD indication is made, the system responds automatically so as to take initial steps to treat the condition. Thus, in one embodiment, the control of pacing rate is altered so as to be better responsive to patient exercise. In another embodiment, 3- or 4-chamber pacing is initiated. In yet another embodiment, drug therapy is automatically administered.

17 Claims, 5 Drawing Sheets

CARDIAC TREATMENT SYSTEM AND METHOD FOR SENSING AND RESPONDING TO HEART FAILURE

FIELD OF THE INVENTION

This invention relates to cardiac pacemakers and cardiac diagnostic devices and, more particularly, such implantable devices having the capability of automatically determining the onset or progression of heart failure, e.g., left ventricular dysfunction, and for delivering an appropriate therapy.

BACKGROUND

The problem of treating patients with heart failure is gaining increasing attention. Such heart failure may be manifested as left ventricular dysfunction (LVD), congestive heart failure (CHF), or other forms. For patients with LVD, the ejection fraction from the left ventricle is reduced, and the ability of the stroke volume to respond to exercise is limited. While the disease of the heart may proceed in different ways, the result is a degenerative reduction in cardiac output. For example, LVD may be produced by a degree of left bundle branch block, leading to loss of synchrony between the left atrium and the left ventricle. Whatever the progress of the disease, cardiac output is reduced, and the heart responds so as to increase cardiac output toward a normal level primarily by heart rate increase. The rate increase may be manifested in several different ways, e.g., there may be an increase in the daily lower spontaneous rate, i.e., the nighttime rate when the patient is at rest. Further, the changed conductive patterns which may form the basis of the LVD can lead to changes in the cardiac signal, e.g., an increased width of the depolarization signal, or QRS. Further, since the body is calling for an increase in blood supply, patients with LVD are also known to have elevated levels of catecholamines at rest, which induces a higher heart rate at rest. In turn, the QT interval for such a patient is affected by the catecholamine level, and thus has a changed pattern during exercise as well. These patients have a decreased QT response, or smaller change in QT, during exercise, such that the QT interval shortening during exercise is smaller than that found normally. Although QT interval is influenced independently by heart rate alone, as well as by exercise and catecholemines, it is not known to what extent each of these factors or both are responsible for the changed QT response to exercise in LVD patients. However, it is known that patients with LVD clearly have a different pattern of QT interval shortening during exercise.

As a consequence of the above observations, the basis for this invention is obtaining information from cardiac signals for deriving an indication of LVD, or onset of LVD. It is seen that for an implanted device such as a cardiac pacemaker, which can sense cardiac signals and process heart rate (or R—R interval), QT interval, and QRS length, as well as QRS and P-wave morphology, information can be obtained for tracking changes in left ventricular function, and in particular for indicating progression toward some degree, or form of left ventricular dysfunction. In particular, a rate responsive pacemaker which uses QT interval as the rate indicating parameter, such as pacemakers made by Vitatron Medical, the assignee of this invention, can be adapted to provide information relating to left ventricular hemodynamic performance, and for indicating the onset of LVD. In such a QT rate responsive pacemaker, there is provided an algorithm for automatically adjusting the rate responsive parameters, i.e., the correlation function between QT and desired rate. This adjustment is suitably done on a daily basis where the pacemaker measures a slope of the correlation function at the lower rate limit, and adjusts the QT-rate function between lower rate limit (LRL) and upper rate limit (URL) accordingly. See U.S. Pat. No. 4,972,834, incorporated herein by reference. If such changes are stored and analyzed for a trend, progress toward LVD can be indicated. Likewise, if it is found that the patient heart rate is not dropped to the programmed LRL during nighttime, such that the spontaneous lower rate has had an upward progression, this trend can also be used as an indicator of the onset of LVD.

Since LVD is generally symptomatic of cardiac conduction disorders, other variations in sensed cardiac signals may also be used for making an indication of LVD, or for corroborating progression toward LVD. For example, in a patient with onset of LVD, the evoked T-wave amplitude may not increase in a normal manner during exercise. Thus, in normal patients with healthy hearts the evoked T-wave amplitude increases up to about fifty percent during exercise, an increase which may correlate with stroke volume. A change in the variation of T-wave amplitude with respect to exercise, and consequent heart rate, can be easily measured and tracked in a QT rate responsive pacemaker, or any pacemaker adapted to sense and recover the T-waves. Likewise, as noted above, changes in QRS duration (width) and/or morphology may also be detected and tracked for detection of a trend.

What is needed in patients with progressive LVD or other types of heart failure is the availability of data from which a cardiologist can properly and accurately chart the progression, determine the nature of the heart failure, and be able to implement the optimal treatment in a timely fashion. Thus, physicians need a better means of diagnosing development of, or onset of LVD, in order to provide appropriate treatment. Modern pacemakers, and indeed even 4 chamber pacemakers for treating heart failure by bi-ventricular pacing, have heretofore not provided any such means for collecting data concerning the onset of LVD. Rather, the procedure has been essentially limited to direct examinations of the patient, which are time consuming and costly, and which cannot be repeated with a desired frequency so as to provide accurate trend information.

Another problem existing in the art today is that patients with implanted DDD pacemakers who develop LVD, may be in a situation where ventricular pacing produces a deleterious effect. Thus, if the pacing may cause a mechanical activation sequence which is abnormal, in which case it would reduce the cardiac output. For example, in patients having left bundle branch block, it has been reported that with normal pacing there may be risk in aggravating activation sequences. See "Four Chamber Pacing in Dilated Cardiomyopathy," Cazeaq et al., PACE, Vol. 17, November 1994, Part II.

In view of the above, it is seen that there is a substantial need in the art for a pacemaker or other implanted device having the capacity to identify the onset of cardiac heart failure, and in particular LVD, and to provide such indication to the patient and the patient's physician, or to provide for an appropriate automatic response to treat the changing patient condition.

SUMMARY OF THE INVENTION

In view of the above need, it is an object of this invention to provide a system and method for monitoring patient cardiac signals and processing such signals to provide data from which the onset or progression of heart failure is determined. While the invention is illustrated primarily by reference to LVD, it is to be understood that it is applicable to various forms of heart failure, including left heart conduction disorders such as LBBB, and other forms of heart dysfunction.

In a preferred embodiment, the system is an implantable cardiac pacing system having a pacemaker and a lead for delivering pacing pulses to and receiving cardiac signals from at least the patient's right ventricle. The pacemaker system may also include a lead for delivery of pacing stimuli to the left ventricle and/or the left atrium in response to an indication of heart failure such as LVD, or a drug dispensing system for dispensing an appropriate drug for treating the heart failure.

For the pacemaker embodiment of this invention, the pacemaker is preferably a rate responsive pacemaker, having one or more sensors for sensing a parameter indicative of pacing rate, and for pacing the patient on demand between a lower rate limit and an upper rate limit. In a specific Embodiment, the pacemaker determines QT interval, and stores data representative of changes in QT interval as a function of heart rate paced and/or spontaneous as well as the patient's spontaneous lower rate when at rest. Variations in the correlation of QT interval and heart rate, and/or variations in patient lower rate at rest are processed to provide a time trend, or profile, from which a determination is made as to whether or not LVD is indicated. In alternate embodiments, other data derived from cardiac signals is processed and stored, e.g., QRS width, T-wave amplitude, etc. Trends in this data are periodically evaluated, e.g., on a daily basis, and stored for downloading to an external programmer or for automatic initiation of a treatment response.

The implanted system may be solely dedicated to detection and storage of cardiac data, and processing of such data to provide an indication of LVD when interrogated. In a more preferred embodiment, the invention is carried out by a system such as a rate responsive pacemaker system which can pace and sense in any combination or all of the four cardiac chambers. The treatment response upon an indication of onset of LVD has a number of embodiments, including changing the rate response function; changing sensor blending for dual or plural sensor rate responsive pacemakers; initiating three or four chamber pacing to achieve improved left heart response, e.g., synchronous ventricular pacing and/or other multi-chamber sequential pacing; and providing for a measured release of an appropriate drug for treating the LVD. In yet another embodiment of the system of this invention, the pacemaker device may be implanted with software for carrying out normal dual chamber pacing, but may be upgraded by programmer downloading to provide different pacing functions, or to function as a three or four chamber pacemaker, along with utilization of an additional lead or leads for delivering stimulus pulses to the left heart chambers.

DESCRIPTION OF THE PREFERRED EMBODIMENTS

Figure 1A:
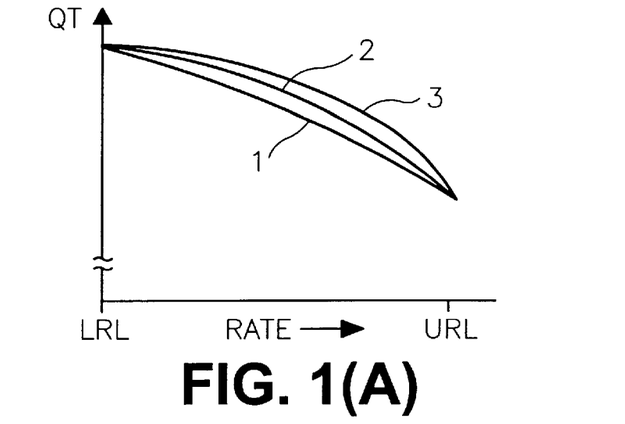
FIG. 1(A) is a diagram illustrating different QT-rate correlation functions for a rate responsive pacemaker.

Referring now to FIG. 1(A), there is shown a set of curves illustrating the relationship between the parameter QT and rate, for a rate responsive pacemaker where QT is the rate-indicating parameter. Thus, each of the curves shown is a separate rateresponsive function, or correlation function for determining rate as a function of sensed QT. Curve 1 is the least aggressive of the curves, in the sense of providing a change in rate for a given change in QT. As seen, curve 2 is somewhat more aggressive, and the third curve is the most aggressive of the three. In a QT pacemaker where the lower rate limit (LRL) and upper rate limit (URL) are programmed to predetermined values, the dynamics of the correlation function can be changed to accommodate sensed changes in the patient QT-rate relationship. See U.S. Pat. No. 4,972,834, hereby incorporated by reference, which shows a technique for adjusting the slope at LRL or URL, where slope is the incremental difference in pacing interval divided by the incremental sensed change in QT. In relation to this invention, it is anticipated that this correlation function will need to be changed in some manner for a patient who receives a pacemaker without significant left ventricular dysfunction, but who later progresses toward some stage of LVD.

Figure 1B:
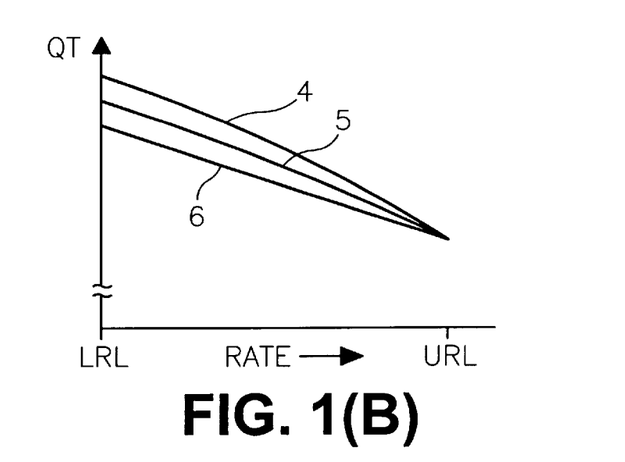
FIG. 1(B) is a diagram illustrating changes in the relationship between QT and rate, as may occur with the onset of LVD.

Referring to FIG. 1B, there is shown a set of curves which indicate a changing relationship between QT and patient heart rate as a patient progresses toward some form of LVD. Curve 4 is presented as a curve for a normal patient, with a first value of QT at LRL (e.g., 70 bpm). After some time and deterioration of normal cardiac function, the curve may change to that shown at 5, corresponding to a smaller QT at LRL. Such a smaller or reduced QT would correspond to the increased catecholamine level, as mentioned, above. Curve 6 represents a condition more advanced toward LVD, showing an even smaller QT at LRL. It is to be seen that if the patient's cardiac condition results in such a changed relationship between QT and heart rate, a QT rate responsive pacemaker that started out with the correlation function represented by curve 4, would need to have the correlation function adjusted in order to correspond to the patient's changed condition.

Figure 1C:
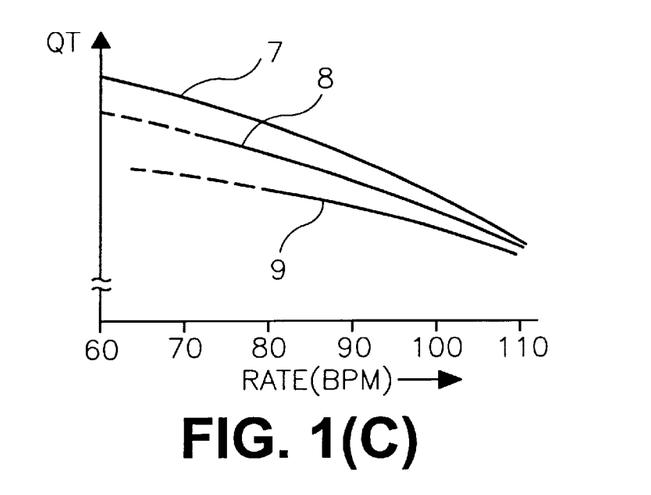
FIG. 1(C) is a set of curves illustrating another way in which the QT-rate relationship may change with the onset of LVD.

Referring to FIG. 1(C), there is shown another set of curves that represents changes in a patient's QT-rate relationship, as the patient progresses toward LVD. Curve 7 is a starting condition which corresponds approximately to curve 4 as seen in FIG. 1B. After some time, it is determined that the patient's QT-rate relationship is as represented by curve 8. As seen, under these conditions, the patient's spontaneous rate does not in fact drop below about 70 bpm, and a different characteristic is exhibited for the relationship between QT and rates of about 70 and an upper limit of about 110 bpm. After even more progression toward LVD, the patient condition is as represented in curve 9, where the patient's lowest spontaneous rate, at nighttime or other rest, is about 80 bpm. Here, in comparing curves 7 and 9, it is seen that there is sufficient difference in the QT-rate relationship for the patient that it can be concluded that the patient has come to the onset of some form of LVD. Such a conclusion can be derived either by comparing the lowest rate (80 for curve 9, compared with 60 for curve 7), or by comparing the slope of the curves. Thus, comparing curve 9 with curve 7, the change in QT between a rate of 80 and a rate of 110 is significantly less.

Figure 2:
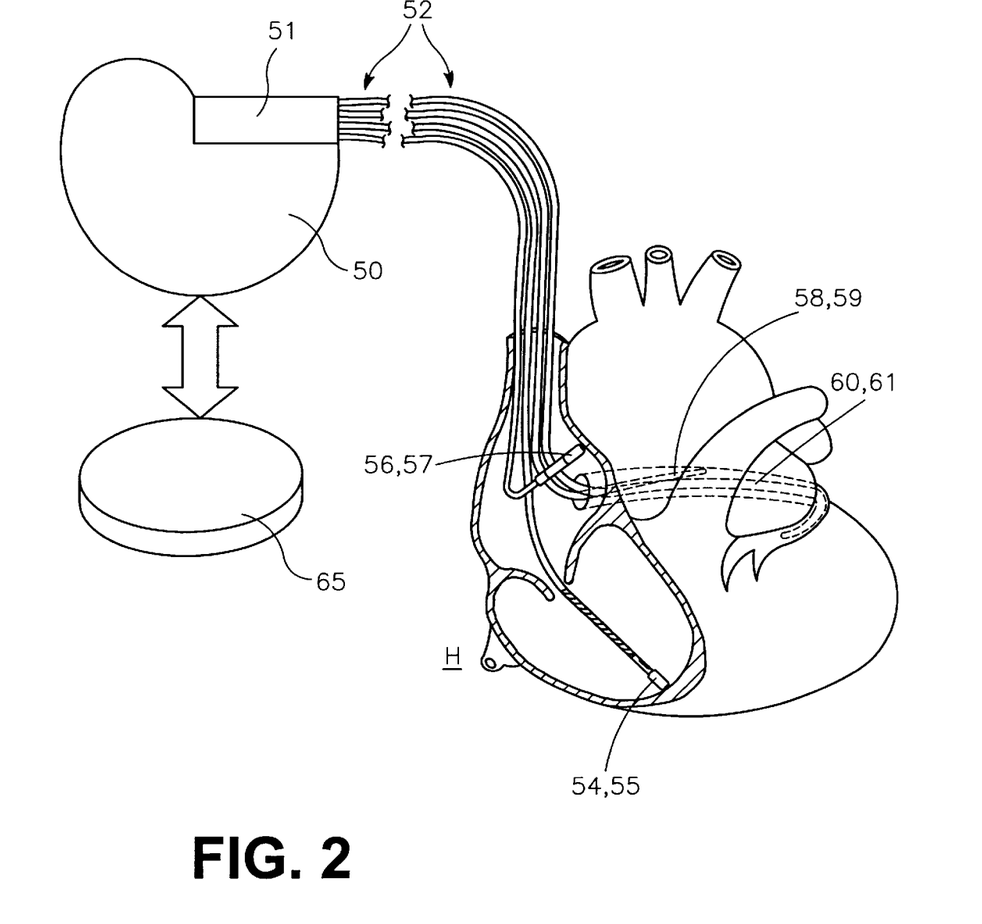
FIG. 2 is a schematic diagram illustrating an implanted pacemaker device and four leads for pacing and sensing in the four cardiac chambers, and also showing a drug dispensing device for supplying a drug for treating a detected form of LVD.

Referring now to FIG. 2, there is shown a schematic diagram representing the system of this invention in relation to a patient's heart. A pacemaker, or other implantable device such as a combined pacemaker-cardioverter defibrillator 50, is a standard available pacemaker for generating pacing pulses and for sensing cardiac signals. A connector block 51 receives the proximal end of four leads, designated at 52, which go to respective locations in the four respective chambers of the heart. It is understood that the invention may normally be practiced with only a dual chamber pacemaker, or even a single chamber (VVI) pacemaker. For a 3- or 4-chamber pacemaker, at the time of implant it may be desired to operate the pacemaker only as a dual chamber pacemaker with lead connections to the right atrium and right ventricle, the pacemaker being adapted to be connected with additional leads for pacing and sensing in the left ventricle and left atrium when and as LVD is determined.

In FIG. 2, a first of the leads is positioned so that its distal tip is in the right ventricle, and carries bipolar electrodes 54, 55. As is known, the lead arrangement may be unipolar, using only a far distal tip lead, in combination with the electrode case as the indifferent lead. A second lead is positioned so that its distal end is in the right atrium, carrying electrodes 56, 57. Another lead is positioned via the coronary sinus for pacing and sensing in the left atrium, having electrodes 58, 59 positioned at about its distal end. A fourth lead is illustrated positioned to pace and sense in the left ventricle, via the coronary sinus and the great vein, having electrodes 60, 61. Although such four-chamber capacity is not necessary for practice of the invention, and indeed detection of LVD can be determined by sensing only signals derived from the right ventricle, a four-chamber system is illustrated so as to indicate the scope of the invention. Additionally, a drug delivery system, shown at 65, is in communication with pacemaker 50, and can be automatically activated to release an appropriate drug for treatment of LVD whenever LVD is detected. The link between the device 50 and the drug dispensing unit 65 may be either by direct wire connection or may be by telemetry.

Figure 3:
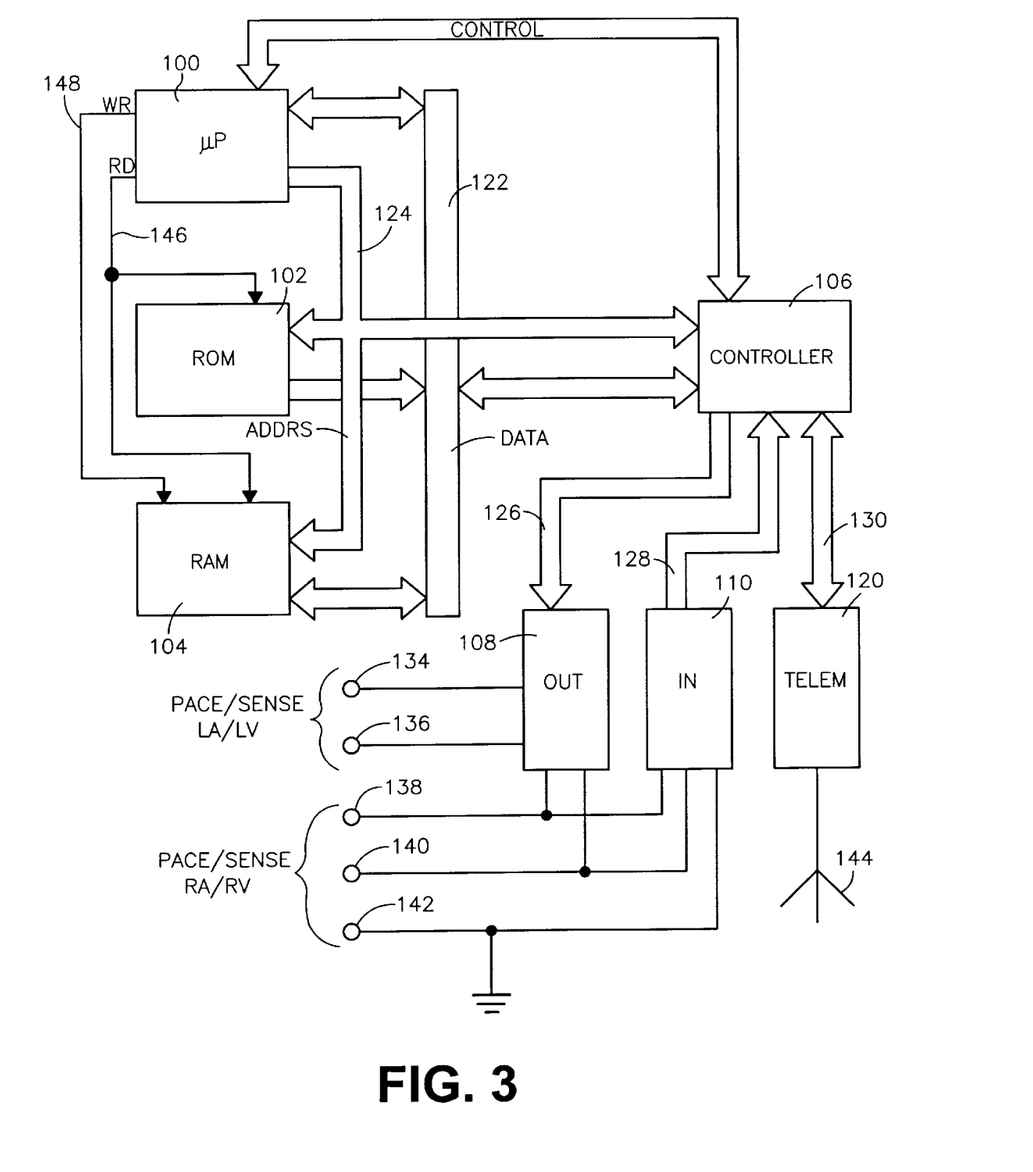
FIG. 3 is a block diagram of a pacemaker incorporating the features of this invention.

FIG. 3 is a functional block diagram of an implantable pacemaker of the type in which the present invention may be practiced. The disclosed embodiment takes the form of a microprocessor controlled device. However, it is believed that the invention might usefully be practiced in other types of devices, including those employing dedicated digital circuitry, and perhaps even in devices comprised primarily of analog timing and control circuitry. As such, FIG. 3 should be considered exemplary, rather than limiting with regard to the scope of applications of the present invention. While the invention is disclosed as embodied in a pacemaker, it is equally applicable to incorporation in a cardioverter, or combined cardioverter pacemaker, or even cardioverter defibrillator pacemaker. While the following discussion of FIG. 3 assumes a single chamber ventricular pacing system, it is to be understood that the invention is applicable to 2-, 3- or 4-chamber systems.

The primary elements of the apparatus illustrated in FIG. 3 are microprocessor 100, read only memory 102, random access memory 104, a digital controller 106, input and output amplifiers 110 and 108 respectively, and a telemetry/programming unit 120. Read only memory 102 stores the basic programming for the device, including the primary instructions set defining the computations performed to derive the various timing intervals performed by the device. Random access memory 104 serves to store the values of variable control parameters, such as programmed pacing rate, pulse widths, pulse amplitudes, and so forth, which are programmed into the device by the physician. Random access memory also stores derived data, such as the cardiac signal data which is used to determine an LVD condition. Reading from random access memory 104 and read only memory 102 is controlled by RD-line 146. Writing to random access memory 104 is controlled by WR-Line 148. In response to a signal on RD-Line 146, the contents of random access memory 104 or read only memory 102 designated by the then present information on address bus 124 are placed on data bus 122. Similarly, in response to a signal on WR-line 148, information on data bus 122 is written into random access memory 104 at the address specified by the information on address bus 124.

Controller 106 performs all of the basic timing and control functions of the device. Controller 106 includes at least one programmable timing counter, initiated on ventricular contractions, paced or sensed, for timing out intervals thereafter. It is also anticipated that the controller 106 would also perform the basic timing functions of the pacing, including 3- or 4-chamber pacing in response to LVD, in accordance with well known techniques. Controller 106 also triggers output pulses from output stage 108 as discussed below, and it generates interrupts on control bus 132 for cyclically waking microprocessor 100 from its sleep state to allow it to perform the required functions. Output circuit 108 is coupled to electrodes 138 and 140 which are employed in a unipolar configuration both for delivery of pacing pulses and for sensing of cardiac signals. Electrode 138 is typically located on the distal tip end of an endocardial lead and is typically placed in the apex of the right ventricle; electrode 140 is placed in the patient's right atrium; and electrode 142 represents the pacemaker housing, which may be used as the indifferent electrode for unipolar pacing and sensing operations. Output circuit 108 is controlled by controller 106 through bus 126 to determine the time, amplitude and pulse width of the pulse to be delivered and to determine which electrode pair will be employed to deliver the pulse.

Sensing of QRS and T-waves is done by input amplifier circuitry, which receives sensed signals from electrodes 138, 142, or from electrodes 54, 55 for a bipolar system. Signals indicating the occurrences of natural ventricular contractions, and paced ventricular contractions as well as T-waves, are provided to the controller 106 via bus 128.

Controller 106 passes data indicative of the occurrence of such ventricular signals to microprocessor 100 via control bus 132, for performance of all necessary calculations, and in particular for timing of the delivery of tachy-inducing pulses in the manner discussed below.

External control of the implanted device is accomplished via telemetry/control block 120, which allows communication between the implanted device and an external programmer (not shown). Radio communication is typically employed via antenna 124. Appropriate telemetry/ programming systems are disclosed in U.S. Pat. No. 4,401, 120, issued to Hartlaub et al., U.S. Pat. No. 4,556,063, issued to Thompson et al., and U.S. Pat. No. 4,550,370, issued to Baker, all of which are incorporated herein by reference in their entireties. However, any conventional telemetry/ programming circuitry is believed workable in the context of the present invention. Information entering the pacemaker from the programmer is passed to controller 106 via bus 130. Similarly, information from the pacemaker is provided to, the telemetry block 120 via bus 130, for transmission to the external programmer.

Also indicated as output from output block 108 are terminals 134 and 136, which may be used in connection with system ground for unilateral pacing or sensing of the left atrium and left ventricle. Again, if bipolar pacing and/or sensing is incorporated, additional electrodes are utilized as illustrated in FIG. 2.

Figure 4:
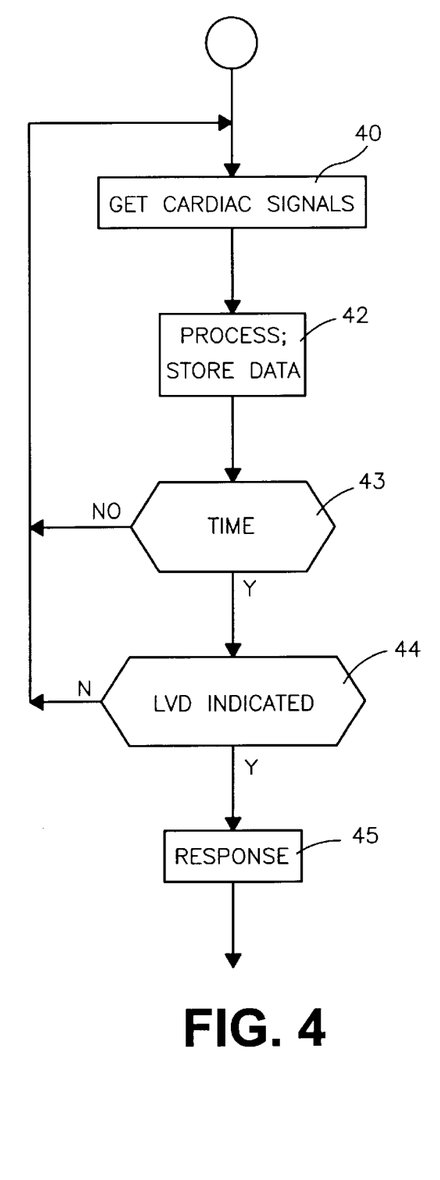
FIG. 4 is a simplified flow diagram showing the primary steps of monitoring cardiac signals, processing the cardiac signals and obtaining and storing data representative of changes in the cardiac signals; identification of onset or progression of LVD; and automatically responding by providing a treatment for the identified LVD.

Referring now to FIG. 4, there is shown a flow diagram primarily of steps taken by a system in accordance with the method of this invention. It is to be understood that these steps are preferably carried out under the control of microprocessor 100, based on software conveniently stored in ROM 102 or RAM 104. In FIG. 4, the first step, as illustrated at 40, is to obtain cardiac signals, which is suitably done each cardiac cycle, or on another convenient basis. In a simple version of the invention, this involves obtaining the QRS signal, or the time of a delivered stimulus; as well as obtaining the T-wave portion of the cardiac signal sensed in the right ventricle. Next, as shown at 42, the cardiac signals are processed, and the resulting data is stored. Thus, the QT time interval is determined and stored; the width or other morphological feature of the QRS portion is determined and stored; and/or the amplitude or other feature of the T-wave is determined and stored. At 43, it is determined whether it is time to analyze the stored data, in order to look for an indication of LVD. For example, the inquiry with respect to LVD may be made daily, or perhaps at longer predetermined intervals. Until this time has been reached, the program simply loops back and, during each cycle, repeats the steps of getting cardiac signals and processing them to obtain data for use in determining LVD. When and if the time period has run out, the program proceeds to step 44, and analyzes the data to determine whether LVD is indicated. This analysis may involve any number of different steps for operating on the data derived from the cardiac signals. Thus, changes in the correlation between QT and heart rate can be analyzed, to see whether the slope is substantially changed, by more than a predetermined amount; whether the low rate at rest has changed more than a predetermined number of bpm compared to a starting rate for the patient; whether the T-wave amplitude varies with rate in the normal rate or in an abnormal manner; whether the QRS width at a given rate has varied, thus indicating a cardiac conduction disorder; etc. If LVD is indicated at 44, the routine branches to 45, for carrying out an appropriate response. This response may be simple, such as setting a flag which can be interrogated by an external programmer for transmitting of data which indicates LVD. Other responses can be automatically undertaken aimed toward initiating treatment of the LVD. These responses can include administering a drug through device 65, in order to treat the condition. In another embodiment an indication of LVD leads to changing the rate response function. For a single sensor rate responsive pacemaker, this entails changing the rate response function so as to accommodate a different reaction to exercise. For a dual sensor rate response system, the response entails altering the blending of the relative influence each of the respective sensor signals. See, for example, U.S. Patent No. 5,065,759, incorporated herein by reference, which discloses a pacemaker where the relative influence of each of a QT signal and an activity signal is adjustable. Further, the response may entail initiation of 3- or 4-chamber pacing, which is directed primarily toward pacing the left ventricle of the heart so as to optimize left ventricular cardiac output. This response can be done automatically where this system incorporates an implanted pacemaker having capacity for providing 3- or 4-chamber pacing. In this situation, or the simpler situation mentioned above where the rate response function is changed, such change can be made by downloading new software for controlling pacemaker functionality into pacemaker memory.

Figure 5:
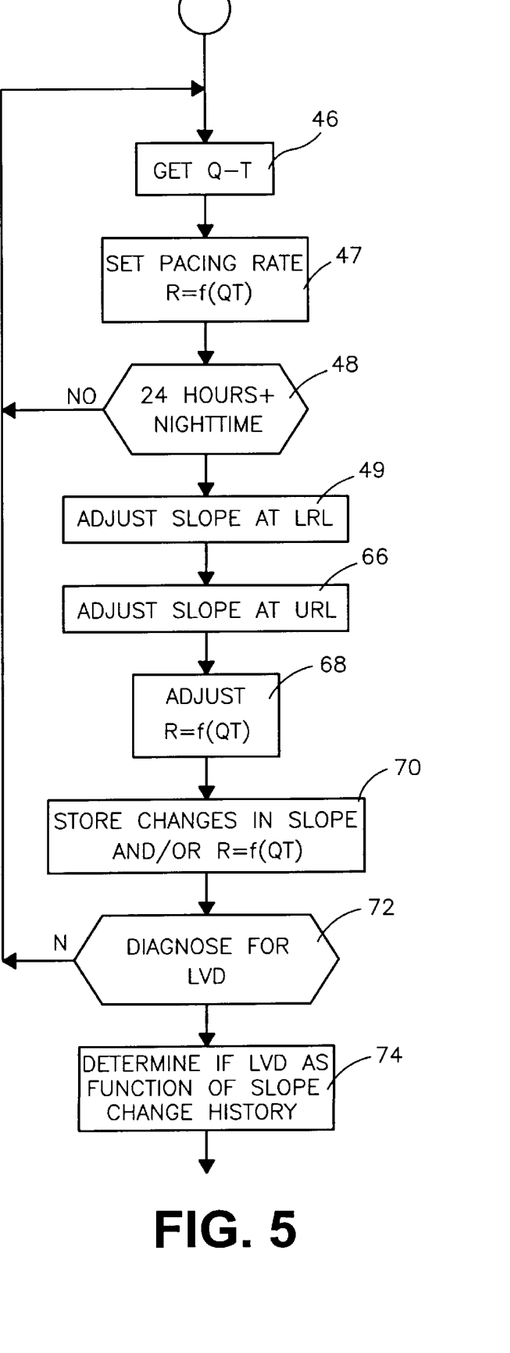
FIG. 5 is a flow diagram illustrating collection of QT-rate data, processing such data to determine changes in the QT-rate correlation, and identification of onset of LVD as a function of determined QT-rate changes.

Referring now to FIG. 5, there is shown a more detailed flow diagram of an embodiment where changes corresponding to QT interval are utilized for determining LVD. The procedure for FIG. 5 is adapted for a QT rate responsive pacemaker, where pacing rate is determined as a function of sensed QT interval. At 46, QT is determined each cycle, and as illustrated at 47, pacing rate is set as a function of QT, i.e., R=f(QT). At 48, it is determined whether it is time to determine whether the rate function should be checked, e.g., is it nighttime and 24 has elapsed since the last check? If yes, at 49 the pacemaker goes through a routine for adjusting the function slope at LRL, as disclosed in incorporated reference U.S. Pat. No. 5,065,759. At block 66, a similar adjustment of the slope at URL can likewise be made. At 68, under the control of the microprocessor, the correlation function R=f (QT) is adjusted to accommodate the changes in slope. At 70, the changes in slope, and/or the change in correlation function, are stored in memory. At 72, it is determined whether the pacemaker should examine the stored data in order to diagnose for an LVD condition. This examination may be made, for example, once a week or once every predetermined period of time. If such a diagnosis is to be made at 74, the data is analyzed to determine whether the changes in slope, or changes in correlation function indicate a trend or a history such as indicates onset of LVD. A simple set of criteria for making this determination can be used, e.g., slope changes exceeding a predetermined limit and in the direction of a smaller QT interval at rest.

Figure 6:
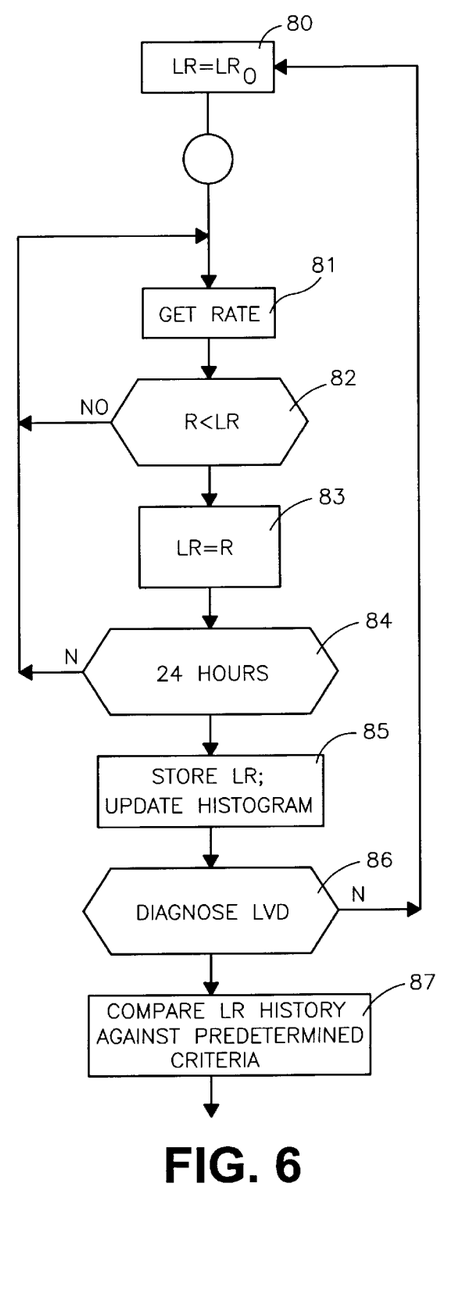
FIG. 6 is a flow diagram of the primary steps carried out by an embodiment of this invention for obtaining measures of nighttime patient lower rate, for accumulating such lower rate data and for identifying LVD as a function of such accumulated lower rate data.

Referring now to FIG. 6, there is shown a flow diagram for determining LVD by examining changes in the lowest heart rate (LR) during a 24 hour period, often the lowest natural rate the patient has during nighttime. At 80, LR is set equal to an initial value, $LR_0$, which is a nominally high rate, i.e., above LRL. At 81, heart rate is determined, and at 82 the rate R is compared to LR. If R is less than LR at 83, LR is set equal to the new value R. At 84, it is determined whether a 24-hour period has passed. If no, the routine goes back to 81 and continues to analyze the rate data, on a cycle-by-cycle basis. When the 24-hour, or daily time period has elapsed, at 85 the value of LR for the last day is stored. This is conveniently done by updating a histogram in memory which provides easily stored data giving a profile of different values of LR. At 86, it is determined whether there should be a diagnosis of LVD, i.e., has enough time passed since the last diagnosis? If no, the routine branches back to 80, resets LR, and continues with the data collection process. If, at 86, it is determined that LVD is to be diagnosed, then at 87 the LR data is compared against predetermined criteria. For example, and referring FIG. 1(C), if the data shows that the majority of LR readings has progressed from 60 to 80, or any other predetermined value relative to the starting point, this is taken as an indication of LVD, or at least a form of LVD requiring a response.

Figure 7:
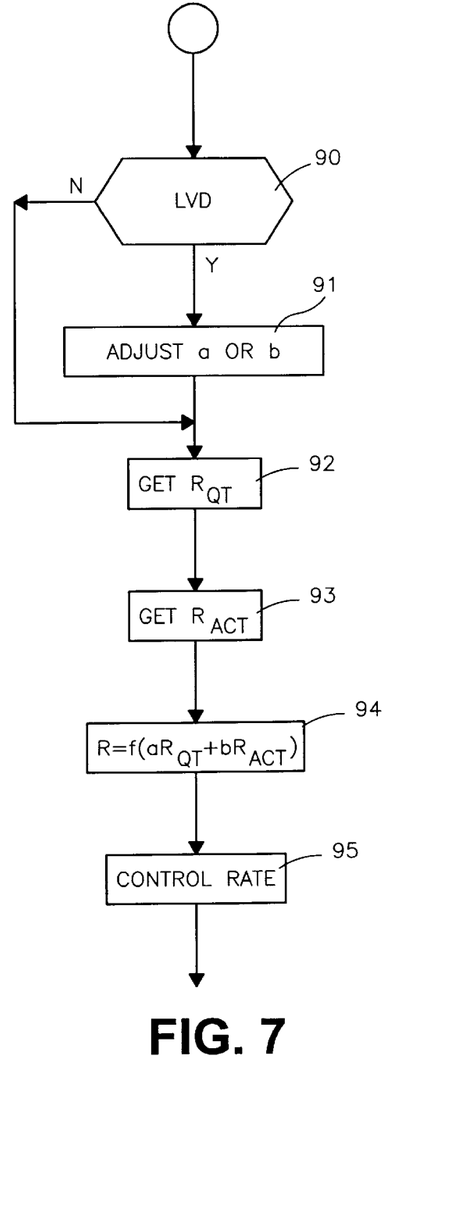
FIG. 7 is a flow diagram illustrating the primary steps in responding to an indication of LVD by adjusting the blended response of a dual sensor rate responsive pacemaker, so as to optimize pacing rate response to exercise for an LVD patient.

Referring now to FIG. 7, there is shown a flow diagram illustrating the primary steps of an algorithm for responding to a determination of LVD in a dual sensor pacemaker. Reference is again made to U.S. Pat. No. 5,065,759, which illustrates a dual chamber pacemaker for controlling pacing rate as a function of QT interval, and an activity signal (ACT) derived from an activity sensor. In such a dual sensor pacemaker, the relative contribution of each of two or more rate-indicating parameters which are sensed by the pacemaker can be adjusted, or "blended." In the case of a combined QT-ACT pacemaker, it is known that the ACT sensor provides a faster but relatively less physiological response, whereas the QT interval provides a slower time response but a more physiological response to body changes. For a patient with LVD, it would be indicated to increase the relative influence or weight of the QT parameter, to provide a relatively slower response to changes in QT interval during exercise.

As seen in FIG. 7, at the start of this routine, it is determined whether there has been an indication of LVD, as shown at 90. If no, the routine skips to block 92. However, if there has been a determination of LVD, then at block 91, either one or both of weight factors a and b is adjusted to provide an overall rate response which is adapted to provide a more appropriate rate response for a patient with an LVD condition. At 92, the pacemaker gets the determination of the rate indicated by the QT which has just been determined, which rate is shown as $R_{QT}$. At 93, the routine determines $R_{ACT}$, which is the rate indicated by the activity sensor. At 94, the pacing rate R is determined as a function of $aR_{QT}+bR_{ACT}$, where $b=a-1$, and a and b thus designate the relative influences of the two sensors. At 95, the pacemaker proceeds to control rate by setting the pacing interval in accordance with the composite rate response function. It is seen that in this way, by adapting the blending of two or more sensors, a more appropriate response to an LVD condition can be obtained and carried out automatically.

It is seen that this invention provides for determining a condition of heart failure such as LVD in a patient, by examination of cardiac signals. The scope of this invention reaches to processing any portion or portions of cardiac signals, from the RV or other chambers, to obtain information indicative of LVD. Thus, while the preferred embodiment has been illustrated in terms of monitoring QT interval variations, other signal variations can be examined, e.g., QRS or T-wave width, amplitude or morphology. By comparing such cardiac signals or signal portions to predetermined criteria, a conventional pacemaker, or one adapted to treat heart failure, can be provided with the capability of identifying the onset or progression of the condition, and enabling an early treatment response.

Upon a determination of heart failure, the treatment response should be particularized for the individual patient, and can include changing the rate response algorithm, bi-ventricular pacing or other multi-chamber pacing, administration of drugs, etc.

What is claimed is:

1. An implantable system for pacing a patient's heart and for determining a condition of heart failure, comprising:
   stimulus means for generating and delivering stimulus pulses to said patient's heart;
   heart signal means for monitoring patient heart signals and collecting heart signal data relating to said heart signals;
   process means for processing said heart signal data to find changes in predetermined features of said heart signals;
   indication means for providing an indication of heart failure as a function of said heart signal changes; and
   response means for automatically responding to said heart failure indication by providing a treatment for said heart failure,
   wherein said response means comprises pacing control means for controlling said stimulus means to deliver pacing pulses in accordance with a predetermined routine adapted to said heart failure condition and, wherein said stimulus means comprises bi-ventricular means for delivering pacing pulses to at least said patient's left and right ventricles, and wherein said control means comprises means for timing delivery of pacing pulses to said patient left and right ventricles so as to improve cardiac output.

2. The pacemaker as described in claim 1, wherein said process means comprises rate means for determining and storing data representative of variations in the patient's heart rate and wherein said rate means comprises means for determining and storing data representative of the patient's lowest heart rate over a predetermined time duration.

3. The system as described in claim 2, wherein said indication means comprises means for comparing said patient lowest heart rate with predetermined criteria, and for indicating onset of LVD as a function of said comparison.

4. An implantable system for pacing a patient's heart and for determining a condition of heart failure, comprising:
   stimulus means for generating and delivering stimulus pulses to said patient's heart;
   heart signal means for monitoring patient heart signals and collecting heart signal data relating to said heart signals;
   process means for processing said heart signal data to find changes in predetermined features of said heart signals;
   indication means for providing an indication of heart failure as a function of said heart signal changes; and
   response means for automatically responding to said heart failure indication by providing a treatment for said heart failure, wherein said monitoring means comprises means for determining the QT interval corresponding to patient heartbeats, said process means comprises means for determining variations of said QT interval with patient heart rate, and said indication means comprises means for indicating an LVD condition as a function of said variations of QT interval with heart rate.

5. An implantable system for pacing a patient's heart and for determining a condition of heart failure, comprising:
   stimulus means for generating and delivering stimulus pulses to said patient's heart;
   heart signal means for monitoring patient heart signals and collecting heart signal data relating to said heart signals;
   process means for processing said heart signal data to find changes in predetermined features of said heart signals;

indication means for providing an indication of heart failure as a function of said heart signal changes; and response means for automatically responding to said heart failure indication by providing a treatment for said heart failure, wherein said process means comprises means for finding changes in morphology of a portion of a patient heart signals, and said indication means comprises means for determining when said changes indicate a progression of heart failure.

6. An implantable pacing system for pacing a patient's heart and for diagnosing heart conditions representative of a form of left ventricular dysfunction (LVD), having a pacemaker, and lead means for sensing cardiac signals from said patient's heart and for delivering said sensed signals to said pacemaker and for delivering pacing pulses from said pacemaker to said heart, said pacemaker comprising:

pace pulse means for generating pacing pulses;

signal means for processing said sensed cardiac signals to obtain information representative of predetermined portions of said signals for use in diagnosing whether said patient has a form of LVD; and diagnosing means for diagnosing when said patient has a form of LVD as a function of said obtained information.

7. The system as described in claim 6, wherein said signal means comprises rate means for determining variations in said patient's heart rate and for storing information relating to said variations.

8. The system as described in claim 6, wherein said signal means comprises rest means for determining variations in patient heart rate while said patient is at rest.

9. The system as described in claim 6, wherein said signal means comprises QT means for determining values of Q-T interval corresponding to different patient heart rates, and storage means for storing data representative of corresponding Q-T intervals and heart rates.

10. The system as described in claim 9, wherein said diagnosing means comprises means for determining changes in the relationship of heart rate and Q-T interval for said patient over a range of heart rates.

11. The system as describe in claim 6, wherein said signal means comprises means for determining Q-T interval, and further comprising rate responsive means for controlling the rate of generation and delivery of pace pulses in accordance with a correlation function of Q-T interval.

12. The system as described in claim 11, comprising means for automatically adjusting said correlation function in order to adapt to changing patient cardiac conditions, and wherein said diagnosing means comprises means for determining changes in said correlation function indicative of a form of LVD.

13. The system as described in claim 6, wherein said patient further comprises rate responsive means for controlling the rate of generation and delivery of pacing pulses as a function of at least one patient parameter, and adjusting means for adjusting said function in response to a diagnosis of a form of LVD.

14. The system as described in claim 6, further comprising rate responsive means for controlling the rate of generated pacing pulses as a function of at least two rate-indicating parameters, weight means for weighing the relative influence of each of said two parameters, and weight adjusting means for adjusting said relative influence in response to a diagnosis of a form of LVD.

15. The system as described in claim 14, wherein said rate responsive means comprises means for controlling rate as a function of patient Q-T interval and a second predetermined parameter, and wherein said weight adjusting means increases the relative influence of Q-T interval in response to a diagnosis of a form of LVD.

16. The system as described in claim 6, wherein said lead means comprises a lead for delivering pacing pulses to said patient's right heart and another lead for delivering pacing pulses to said patient's left heart, and said pace pulse means comprises means for generating pulses for deliver to both said left and right hearts in response to a diagnosis of a form of LVD.

17. The system as described in claim 6, comprising drug delivery means for delivering a dose of drug for treatment of LVD in response to a diagnosis of a form of LVD.

* * * * *